Figure 1:
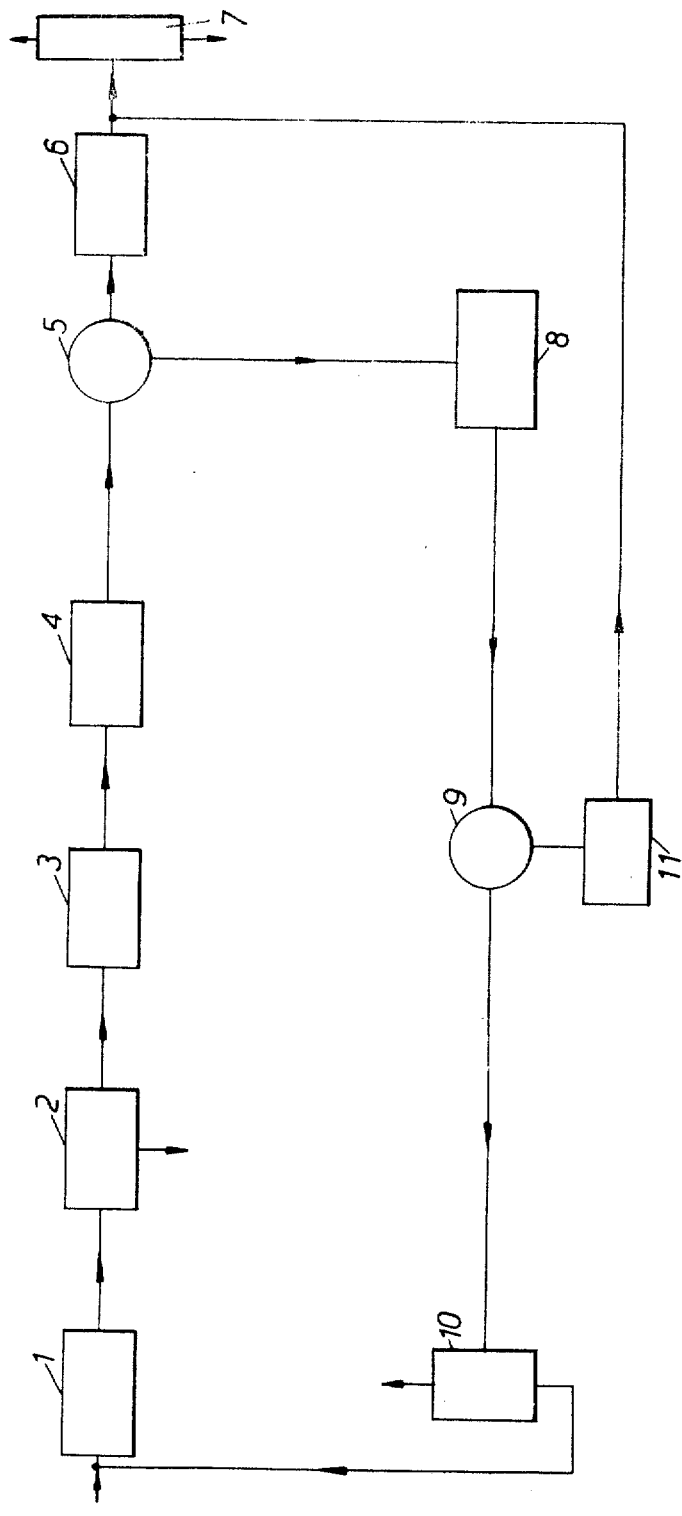

United States Patent [19]

Lindley et al.

[11] 3,959,978

[45] June 1, 1976

[54] SEPARATION PROCESS BY FRACTIONAL CRYSTALLIZATION

[75] Inventors: John Lindley; Andrew John McLeod, both of Stockton-on-Tees, England

[73] Assignee: Imperial Chemical Industries Limited, London, England

[22] Filed: Apr. 25, 1972

[21] Appl. No.: 247,304

[30] Foreign Application Priority Data
Apr. 30, 1971 United Kingdom............. 12337/71

[52] U.S. Cl.............................. 62/58; 260/674 A
[51] Int. Cl.²........................................ B01D 9/04
[58] Field of Search........................................ 62/58

[56] References Cited
UNITED STATES PATENTS

| | | | |
|---|---|---|---|
| 2,672,487 | 3/1954 | Tegge et al. | 62/58 |
| 2,886,587 | 5/1959 | Kolner | 62/58 |
| 2,945,903 | 7/1960 | Findlay | 62/58 |
| 2,979,453 | 4/1961 | Kiersted et al. | 62/58 |
| 3,050,952 | 8/1962 | Marwil | 62/58 |
| 3,067,270 | 12/1962 | Weedman | 62/58 |
| 3,216,833 | 11/1965 | McKay et al. | 62/58 |
| 3,283,522 | 11/1966 | Ganiaris | 62/58 |

*Primary Examiner*—Norman Yudkoff
*Assistant Examiner*—J. Sofer
*Attorney, Agent, or Firm*—Cushman, Darby & Cushman

[57] ABSTRACT

A crystallisable component, for example paraxylene, is separated from solution by chilling, separating crystals, washing them, chilling the mother liquor in the presence of wash liquid, separating further crystals and washing them. The invention enables concentrated solutions to be handled easily by keeping the proportions of crystals at each crystallisation stage low without requiring two separations of wash liquid from mother liquor.

9 Claims, 1 Drawing Figure

SEPARATION PROCESS BY FRACTIONAL CRYSTALLIZATION

This invention relates to a separation process.

It is known to separate crystallisable components from solutions by chilling the solutions and separating crystals of the component in, for example, centrifuges or filters. It is also known to wash such crystals with a wash liquid, which is normally chosen so as to be miscible with the mother liquor, not to dissolve an excessive proportion of the crystallised component, and to be readily separable from the mother liquor especially by distillation. In the separation of paraxylene from mixtures thereof with at least one other xylene and/or ethyl benzene, suitable wash liquids are, for example, alcohols having 1 to 3 carbon atoms, especially methanol and paraffins or cycloparaffins having 4 to 6 carbon atoms, especially pentane, including normal and isopentane.

If the solution to be treated comprises a high proportion of the crystalisable component and is chilled to a temperature at which a large proportion of the crystallisable component is crystallised, a slurry will be produced which is difficult to handle; e.g. pipes carrying the slurry may tend to block and pumps may be unable to move it efficiently. If on the other hand, a lesser degree of chilling is used, part of the crystallisable component will not be recovered.

According to this invention a crystallisable component is separated from a solution thereof by chilling the solution to crystallise part of the component, separating crystals of the component from a mother liquor, washing the separated crystals with a suitable wash liquid, chilling the mother liquor in the presence of at least part of the wash liquid to produce further crystals of the crystallisable component, separating such further crystals of the crystallisable component, washing the crystals thus separated with further wash liquid and separating wash liquid from the separated crystallisable component.

This invention enables a large proportion of the crystallisable component to be recovered from concentrated solutions without requiring the handling of thick slurries and also has the advantage that there is no need to chill the crystallisable component which is separated first to the temperature reached in producing the further crystals.

In the recovery of paraxylene from mixtures comprising at least one other xylene and/or ethyl benzene it is usual to cool the mixture to a temperature at which paraxylene crystallises and to treat the resulting slurry, i.e. mixture of crystals and mother liquor (for example by filtering or centrifuging it or by processing it in a counter-current washing apparatus) so as to recover the paraxylene at least partially separated from the remaining components.

Mixtures of paraxylene with other xylenes and/or ethyl benzene commonly contain at most 25% by weight of paraxylene and large quantities of metaxylene. Because of the formation of eutectics with o- or m-xylene it is difficult to reduce the paraxylene content below 8% and to reach this figure it is necessary to chill to temperatures of, for example, −68.5°C. Many users of paraxylene require it to be of high purity (for example, 99% purity or better) and it is extremely difficult to obtain paraxylene in an adequate state of purity by a single crystallisation step. For this reason the first formed crystals may be separated, for example, by filtering or centrifuging. The mother liquor may be isomerised to increase its paraxylene content thus enabling more paraxylene to be recovered from it. The crystals may be melted to give a mixture comprising, for example, 50 to 99%, preferably 50 to 85%, and more preferably 60 to 80% by weight of paraxylene and recrystallised, the new crystals being then recovered by filtering or centrifuging.

The invention is particularly appropriate to the separation of paraxylene from mixtures thereof with at least one other xylene and/or ethyl benzene, which mixtures may comprise, for example 50 to 98% by weight of paraxylene, and preferably comprise 50 to 85%, and more preferably 60 to 80% by weight of paraxylene.

When such mixtures are treated in the process they may be conveniently chilled to a temperature in the range −30° to −10°C to form a slurry containing paraxylene crystals and a mother liquor, separating the crystals, for example by centrifuging, washing the crystals with a suitable wash liquid, for example pentane, methanol or mixtures of methanol and water, chilling the mother liquor in the presence of wash liquid to −40° to −60°C to produce a slurry containing further paraxylene crystals and a mother liquor, filtering to separate the further paraxylene crystals, and washing the further paraxylene crystals with a suitable wash liquid. The wash liquid is preferably the same for both yields of crystals.

The paraxylene crystals of both of the above stages are preferably freed from wash liquid, suitably by distillation. The mother liquor which may contain 12 to 40%, for example 15 to 25% by weight of paraxylene may, after separation from wash liquid by distillation, be processed together with incoming mixtures of paraxylene with other xylenes and/or ethyl benzene containing at most 30%, and preferably at most 25%, by weight of paraxylene to yield more of the mixture comprising, for example, 50 to 98%, and preferably 50 to 85% by weight of paraxylene. Mother liquor from this separation may be isomerised to increase its paraxylene content so that it may be re-used. If this is done it is normally desirable to distill it to separate compounds other than $C_8$ aromatics (principally benzene, toluene and $C_9$ aromatic compounds) from it. If toluene is used as a wash liquid, isomerisate may be fed together with recycled mother liquor containing toluene wash liquid and optionally also with incoming fresh feed to a still which removes the toluene.

The wash liquid may be supplied at a rate of 1 to 50%, and preferably 5 to 20% by weight, of the crystals being washed. It is preferred that it should constitute at most 30%, and more preferably at most 20% of the mother liquor at any stage.

One form of the invention will now be described with reference to FIG. 1 which shows a flowsheet of a plant for operating the process of the invention.

A feedstock which is a mixture of xylenes and ethyl benzene of composition 16% paraxylene, 50% metaxylene, 25% orthoxylene, 7% ethyl benzene and 2% of mainly other aromatic compounds by weight is cooled to −68°C in chillers (1) to produce a slurry containing 9½% of paraxylene crystals by weight. The slurry is filtered in filter (2) and the crystals passed to melt tank (3) in which a solution, containing 70% by weight of paraxylene, is formed. Mother liquor is passed from the filter (2) to an isomerisation plant to produce fresh feedstock.

The solution from melt tank (3) is cooled in chillers (4) to a temperature of −15°C thus producing a slurry containing 44% by weight of paraxylene crystals. This slurry is then passed to continuous centrifuge (5) in which the crystals are separated and washed with 10% of their own weight of n-pentane. The washed crystals are melted in melt tank (6) and distilled in still (7) to remove pentane. The mother liquor from continuous centrifuge (5) which contains 4% by weight of pentane and 50% by weight of paraxylene is passed to chiller (8) in which it is cooled to −50°C thus producing a slurry containing 41% by weight of paraxylene crystals. This slurry is then separated in a cyclic batch centrifuge (9) and the crystals washed with 10% of their weight of n-pentane. The crystals are removed and fed to melt tank (11) from which a melt is passed to still (7). Mother liquor from centrifuge (9) containing 20% by weight of paraxylene is fed to still (10) where pentane is removed and then passed to chiller (1).

Figure 2:
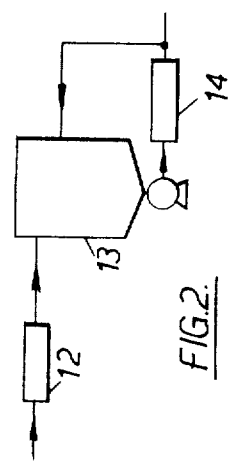

Chillers (1) and (8) are shown in greater detail in FIG. 2. Each comprises a scraped surface chiller (12) feeding a residence tank (13) which is provided with a loop circulating slurry contained in it through a further scraped surface chiller (14) from the outlet of which the chilled slurry is passed to the next section of the plant.

Heat exchangers are provided where appropriate to improve the thermodynamic efficiency of the plant.

The paraxylene recovered from still (7) is found to be of 99.5% purity.

It is preferred in this invention that the slurries handled should contain at most 50% by weight of crystals, and more preferably at most 45% by weight.

What is claimed is:

1. A process in which paraxylene is separated from a solution comprising paraxylene and at least one other xylene, ethyl benzene, or a mixture of at least one other xylene and ethyl benzene by chilling the solution to a temperature in the range of −30° to −10°C to crystallise part of the paraxylene, separating crystals of the paraxylene from the mother liquor, washing the separated crystals with a wash liquid, chilling the mother liquid in the presence of at least part of the wash liquid to a temperature in the range of −40° to −60°C to produce further crystals of the paraxylene, separating such further crystals of the paraxylene from the mother liquor, washing the crystals thus separated with the wash liquid and separating wash liquid from the separated paraxylene.

2. A process as claimed in claim 1 in which the paraxylene solution which is so processed is a second mixture comprising 50 to 98% by weight of paraxylene obtained from a first mixture comprising the paraxylene, at least one other xylene, ethyl benzene or a mixture of at least one other xylene and ethyl benzene by cooling the first mixture to a temperature at which paraxylene crystallises, treating the resulting mixture of crystals and mother liquor so as to recover paraxylene at least partly separated from the remaining components and melting the crystals thus recovered to give said second mixture comprising 50 to 98% by weight of paraxylene.

3. A process as claimed in claim 2 which comprises chilling the second mixture to a temperature in the range −30° to −10°C to form a slurry containing paraxylene crystals and a mother liquor, separating the crystals by centrifuging, washing the crystals with a wash liquid, chilling the mother liquor in the presence of wash liquid to −40° to −60°C to produce a slurry containing further paraxylene crystals and a mother liquor; separating the further paraxylene crystals by centrifuging and washing the further paraxylene crystals with a wash liquid.

4. A process as claimed in claim 3 in which the wash liquid is the same for both cases.

5. A process as claimed in claim 1 in which the wash liquid is an alcohol having 1 to 3 carbon atoms or a paraffin or cycloparaffin having 4 to 6 carbon atoms.

6. A process as claimed in claim 5 in which the crystallised paraxylene is freed from wash liquid by distillation.

7. A process as claimed in claim 6 in which the mother liquor after separation from wash liquid by distillation is recycled to and processed together with fresh mixtures of paraxylene with other xylenes, ethyl benzene or a mixture of other xylenes and ethyl benzene containing at most 25% by weight paraxylene to yield more of a mixture comprising 50 to 98% by weight of paraxylene.

8. A process as claimed in claim 7 in which,
    after the separation of the mixture comprising 50 to 98% of paraxylene, a remaining mixture is isomerised to increase its paraxylene content for reuse.

9. A process as claimed in claim 1 in which the wash liquid is supplied at a rate of 1 to 50% by weight of the crystals being washed and in which the wash liquor constitutes at most 30% of the mother liquor at any stage.

* * * * *